United States Patent [19]
Dobrovolny

[11] Patent Number: 5,727,899
[45] Date of Patent: Mar. 17, 1998

[54] FULCRUM CLAMP

[75] Inventor: Walter J. Dobrovolny, St. Paul, Minn.

[73] Assignee: Minnesota Scientific, Inc., Minneapolis, Minn.

[21] Appl. No.: 710,210

[22] Filed: Sep. 13, 1996

[51] Int. Cl.⁶ .................................................. A61B 17/02
[52] U.S. Cl. ...................... 403/389; 403/384; 403/DIG. 9
[58] Field of Search .............................. 600/228, 231, 600/233, 234, 230; 24/535, 540, 541, 513–515; 403/389, 391, 384, DIG. 9

[56] References Cited

U.S. PATENT DOCUMENTS

| | | | |
|---|---|---|---|
| 667,735 | 2/1901 | Pease | 24/541 X |
| 2,207,860 | 7/1940 | Hassler | 24/514 X |
| 4,275,872 | 6/1981 | Mullis | 403/389 X |
| 4,421,108 | 12/1983 | Cabrera et al. | 600/234 |
| 4,467,791 | 8/1984 | Cabrera et al. | 600/234 |
| 4,586,221 | 5/1986 | Wu | 24/535 |
| 4,718,151 | 1/1988 | LeVahn et al. | 24/535 |
| 4,949,707 | 8/1990 | LeVahn et al. | 600/234 |
| 5,020,195 | 6/1991 | LeVahn | 24/514 |
| 5,025,780 | 6/1991 | Farley | 600/230 |
| 5,242,240 | 9/1993 | Gorham | 403/391 |

*Primary Examiner*—Anthony Knight
*Attorney, Agent, or Firm*—Kinney & Lange, P.A.

[57] ABSTRACT

A clamping device includes a first clamping member and a second clamping member that are pivotally mounted with respect to each other. The first clamping member is fabricated from a unitary structure. The first clamping member has a first clamping end, a second clamping end, and a first fulcrum portion located between the first clamping end and the first attachment end.

19 Claims, 4 Drawing Sheets

FULCRUM CLAMP

BACKGROUND OF THE INVENTION

The present invention relates generally to a captivated clamp for use in mounting surgical retractors with respect to an operating table. More particularly, the present invention relates to a captivated clamp in which at least one of the clamping members is fabricated from a unitary structure.

When assembling retractor support apparatuses, retractor clamps are commonly used to mount support arms with respect to an operating table and to attach surgical retractors to the support arms. Some retractor clamps are manufactured in a captivated configuration so that users cannot disassemble the retractor clamp.

The retractor clamps typically include a first clamping member, a second clamping member, and a handle. LeVahn et al. U.S. Pat. No. 4,718,151, LeVahn U.S. Pat. No. 5,020,195, and Gorham U.S. Pat. No. 5,242,240, which are all assigned to the assignee of the present application, disclose retractor clamps in which at least one of the clamping members is fabricated from a unitary structure that is generally in the shape of the letter "U". In each of these retractor clamps, the object to be clamped is placed between the legs of the "U"-shaped structure so that the object is proximate to the base of the "U"-shaped structure. Movement of the legs of the "U" towards each other causes the object to be clamped with respect to the clamping member.

SUMMARY OF THE INVENTION

A clamping device includes a first clamping member and a second clamping member that are pivotally mounted together. The first clamping member is fabricated from a unitary structure. The first clamping member has a first clamping end, a first attachment end, and a first fulcrum portion located between the first clamping end and the first attachment end.

DETAILED DESCRIPTION OF THE PREFERRED EMBODIMENTS

Figure 1:
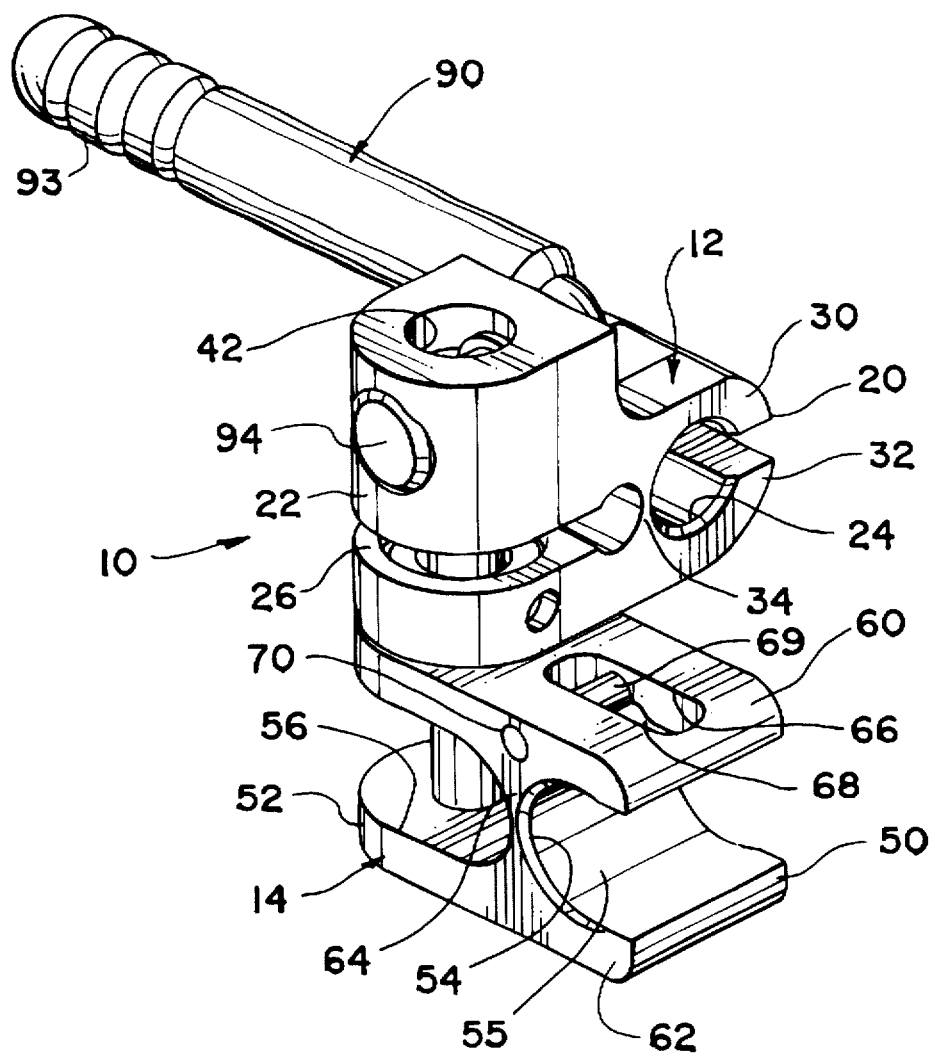
FIG. 1 is a perspective view of clamp according to the present invention.
Figure 2:
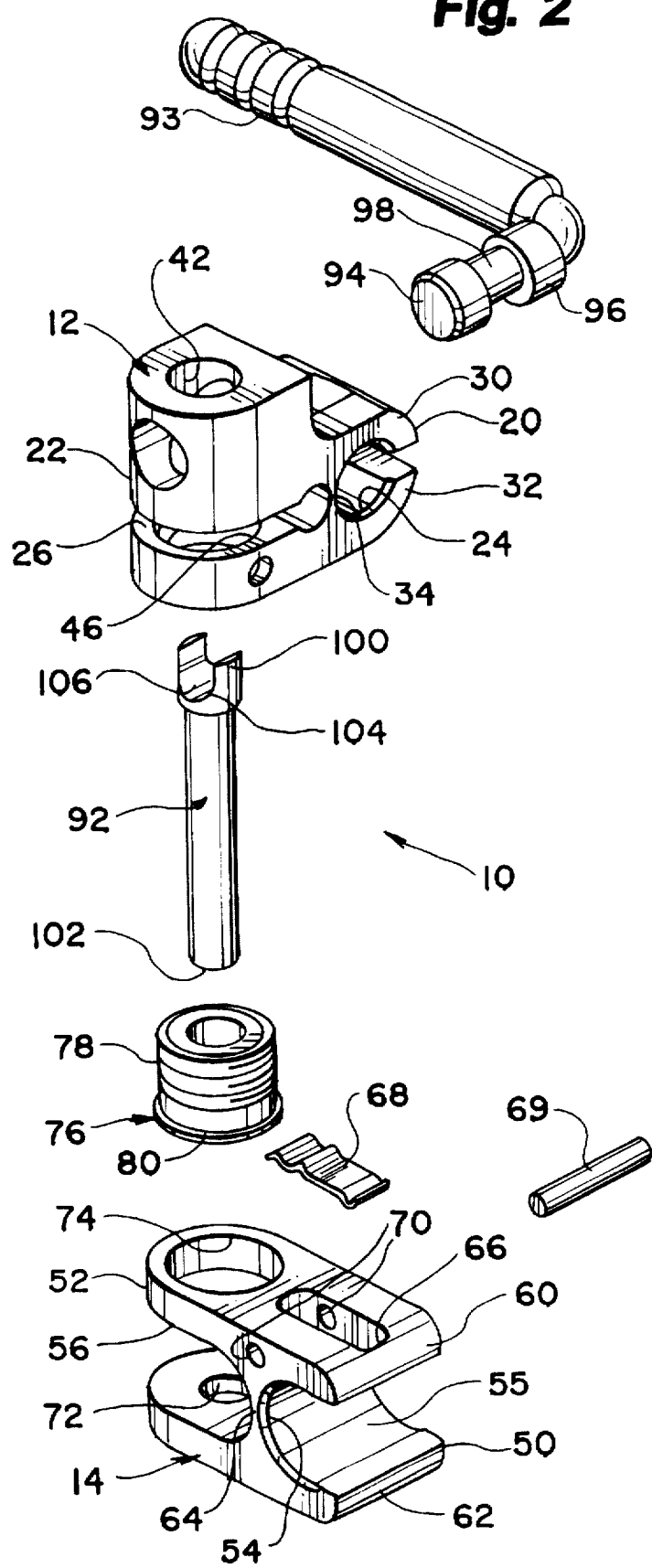
FIG. 2 is an exploded view of the clamp.

A clamp according to the present invention is most clearly illustrated at 10 in FIGS. 1 and 2. The clamp 10 is particularly suited for use in conjunction with mounting retractors with respect to an operating table. The clamp 10 includes a first clamping member 12 and a second clamping member 14.

One of the advantages of the clamp 10 of the present invention is that the second clamping member 14 retains the clamp 10 in a selected position with respect to an object that is to be clamped when the clamp 10 is in a nonclamping position. Retaining the clamp 10 in the selected position while the clamp 10 is in the nonclamping position enhances the ability to use the clamp 10 of the present invention because the clamp 10 does not have to be held in the selected position when positioning an object for clamping in the first clamping member 12.

At least one of the first and second clamping members 12, 14 is preferably constructed from a unitary structure. As used herein, the term "unitary structure" means that the clamping members are fabricated by machining a single piece of material into the desired configuration. Forming the first and second clamping members 12, 14 from a unitary structure enhances the ability to use the clamp 10 while also making the clamp 10 more durable than prior art clamps.

Figure 3:
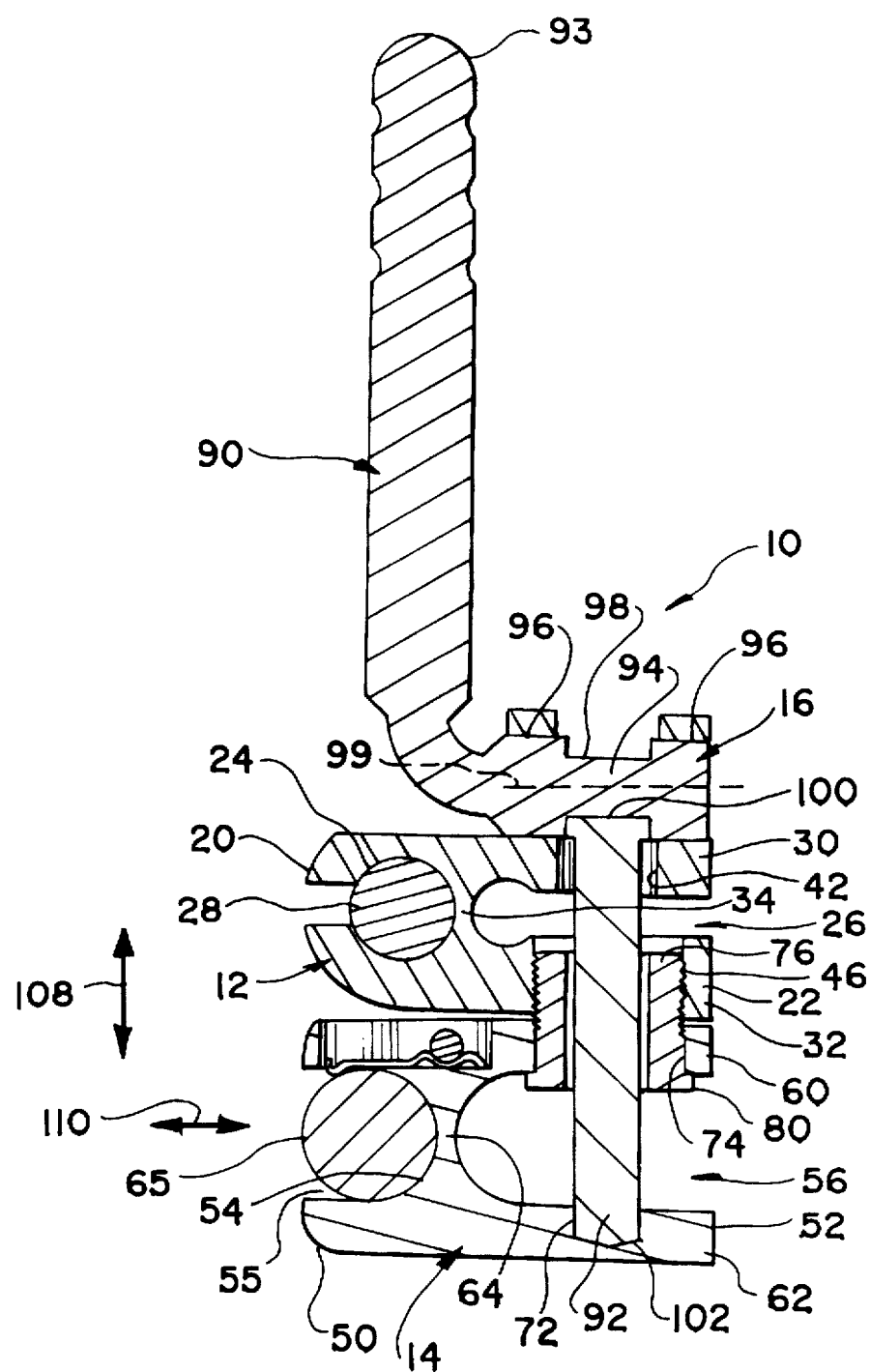
FIG. 3 is a sectional view of the clamp.

The first clamping member 12 has a first clamping end 20 and a first attachment end 22, which is opposite the first clamping end 20. The first clamping member 12 clamps (as illustrated in FIG. 3) a retractor handle 28 of a retractor (not shown) proximate the first clamping end 20. The retractor support is similar to the retractor support shown in U.S. Pat. No. 4,949,707 which is hereby incorporated by reference. The first clamping member 12 is pivotally mounted with respect to the second clamping member 14 proximate the first attachment end 22.

Proximate the first clamping end 20, the first clamping member 12 has a first clamping surface 24 formed therein. To assist in clamping the handle 28 with the first clamping surface 24, the first clamping surface 24 is preferably shaped to substantially extend around the object 28 and to substantially conform with an outer surface of the object 28, as most clearly illustrated in FIG. 3.

Proximate to the first attachment end 22, the first clamping member 12 has a first recess 26 formed therein. The first clamping surface 24 and the first recess 26 generally cause the first clamping member 12 to take the shape of the letter "H" having an upper leg portion 30, a lower leg portion 32, and a fulcrum portion 34, which extends between the upper leg portion 30 and the lower leg portion 32. The fulcrum portion 34 allows the upper leg portion 30 to pivot with respect to the lower leg portion 32. When the upper leg portion 30 is pivoted with respect to lower leg portion 32, it is possible to clamp the handle 28 with the first clamping surface 24.

The first clamping member 12 also includes an actuating rod bore 42 that is in communication with the first recess 26. The actuating rod bore 42 is preferably oriented substantially transverse to the first clamping surface 24. A portion of the actuating rod bore 42 that extends through the lower leg portion 32 preferably has a female threaded region 46.

Similar to the first clamping member 12, the second clamping member 14 has a second clamping end 50 and a second attachment end 52, which is opposite the second clamping end 50. The second clamping member clamps onto a cylindrically shaped portion 65 of a retractor support (not shown) proximate the second clamping end 50. The second clamping member 14 is pivotally mounted with respect to the first clamping member 12 proximate to the second attachment end 52.

Proximate the second clamping end 50, the second clamping member 14 has a second clamping surface 54 formed therein. Proximate the second attachment end 52, the second clamping member 14 has a second recess 56 formed therein. The second clamping surface 54 and the second recess 56 generally cause the second clamping member 14 also to take the shape of the letter "H" having an upper leg portion 60, a lower leg portion 62, and a fulcrum portion 64, which extends between the upper leg portion 60 and the lower leg portion 62. The fulcrum portion 64 allows the upper leg portion 60 to pivot with respect to the lower leg portion 62 so that an object may be clamped with the second clamping surface 54.

The second clamping surface 54 is shaped to conform with the cylindrically shaped portion 65 of the retractor support (not shown). The second clamping surface 54 defines a clamping slot 55. The clamping slot 55 permits placement of the clamp on the retractor support (not shown) without moving any other objects that have been previously clamped. The clamp need not be slid along the support to a new position, but can be removed away from the support detaching the clamp from the retractor support, and move to a new position by placing the clamping slot 55 against the retractor support in a movement perpendicular to the axis of that portion of the retractor support, as indicated by arrow 110 of FIG. 3.

When the clamp 10 is in a nonclamping position, the portion 65 is retained adjacent the second clamping surface 54 with a retaining clip 68, which is preferably formed from a metallic spring material. The retaining clip 68 provides a preliminary clamping force around the portion 65 of the retractor support (not shown) such that it prevents the clamp 10 from rotating when the clamp is in the nonclamping position. Although the retaining clip 68 provides sufficient force to secure the clamp 10 onto the retractor support, the clamp 10 can be removed by using manual force from the retractor support and repositioned or placed elsewhere on the retractor support without the need to move other retractors or devices that are secured to the retractor support.

The second clamping member 14 includes a retaining clip receiving recess 66 that is adapted to receive the retaining clip 68. The retaining clip 68 is retained in the retaining clip receiving recess 66 with a retaining pin 69 that passes through retaining pin apertures 70 formed in the second clamping member 14 on either side of the retaining clip receiving recess 66.

The second clamping member 14 has an actuating rod recess 72 formed into the lower leg portion 62 in the second recess 56. The second clamping member 14 also has a nut bore 74 that extends through the upper leg portion 60 and which is in communication with the second recess 56.

The first clamping member 12 is pivotally attached to the second clamping member 14 with a threaded nut 76. The threaded nut 76 includes a male threaded region 78 that is shaped to conform with the female threaded region 46. The threaded nut 76 further includes an annular lip 80 extending therefrom opposite the male threaded region 76. The annular lip 80 is selected with a diameter that is wider than the nut bore 74 so that the annular lip 80 prevents the threaded nut 76 from passing through the nut bore 74.

The threaded nut 76 maintains all of the components of the clamp in an assembled relationship and thereby prevents problems associated with disassembling and reassembling the clamp. This configuration is referred to as a captivated clamp.

The clamp 10 further includes an actuating mechanism 16 for moving the clamp 10 between a nonclamping position and a clamping position so that objects may be clamped by the first and second clamping members 12, 14. The actuating mechanism 16 includes a clamp handle 90 and an actuating rod 92. The clamp 10 is moved between the open and clamping positions when the clamp handle 90 engages the actuating rod 92 using a camming action.

The clamp handle 90 includes a grip portion 93 and a pivot portion 94, which is preferably oriented substantially perpendicular to the grip portion 93. The pivot portion 94 preferably has a substantially cylindrical outer surface 96 that allows the pivot portion 94 to rotate within the handle bore 44.

The camming action is provided by an eccentric section 98 on the pivot portion 94. The eccentric section 98 is preferably located at an intermediate location on the pivot portion 94, as most clearly illustrated in FIG. 2. The eccentric portion 98 is offset from a central axis 99 of the pivot portion 94, as most clearly illustrated in FIG. 3.

The actuating rod 92 has a first end 100 and a second end 102. The first end 100 includes an arcuate recess 104. The actuating rod 92 engages the clamp handle 90 by contact between a surface 106 of the arcuate recess 104 and the eccentric section 98. The second end 102 engages the second clamping member 14 in the actuating rod recess 72.

In operation, rotation of the clamp handle 90 with respect to the first clamping member 12 causes the pivot portion 94 to rotate in the handle bore 44. Rotation of the pivot portion 94 thereby causes the eccentric section 98 to produce a camming action that causes the actuating rod 92 to be urged toward the second clamping member 14. This movement thereby causes the second end 102 of the actuating rod 92 to force the lower leg portion 62 proximate to the second attachment end 52 apart from the upper leg portion 20 proximate to the first attachment end 22, as indicated by arrow 108 in FIG. 3. This action also causes the upper and lower leg portions 60, 62 proximate to the second clamping end 50 to move towards each other and thereby clamps the portion 65 of the retractor support (not shown) with the second clamping surface 54. This action also causes the upper and lower leg portions 20, 22 proximate to the first clamping end 20 to move towards each other and thereby clamps the handle 28 of the retractor with the first clamping surface 24. Another result of moving the clamp 10 to the clamping position is that the first clamping member 12 is retained in a fixed position with respect to the second clamping member 14.

Figure 4:
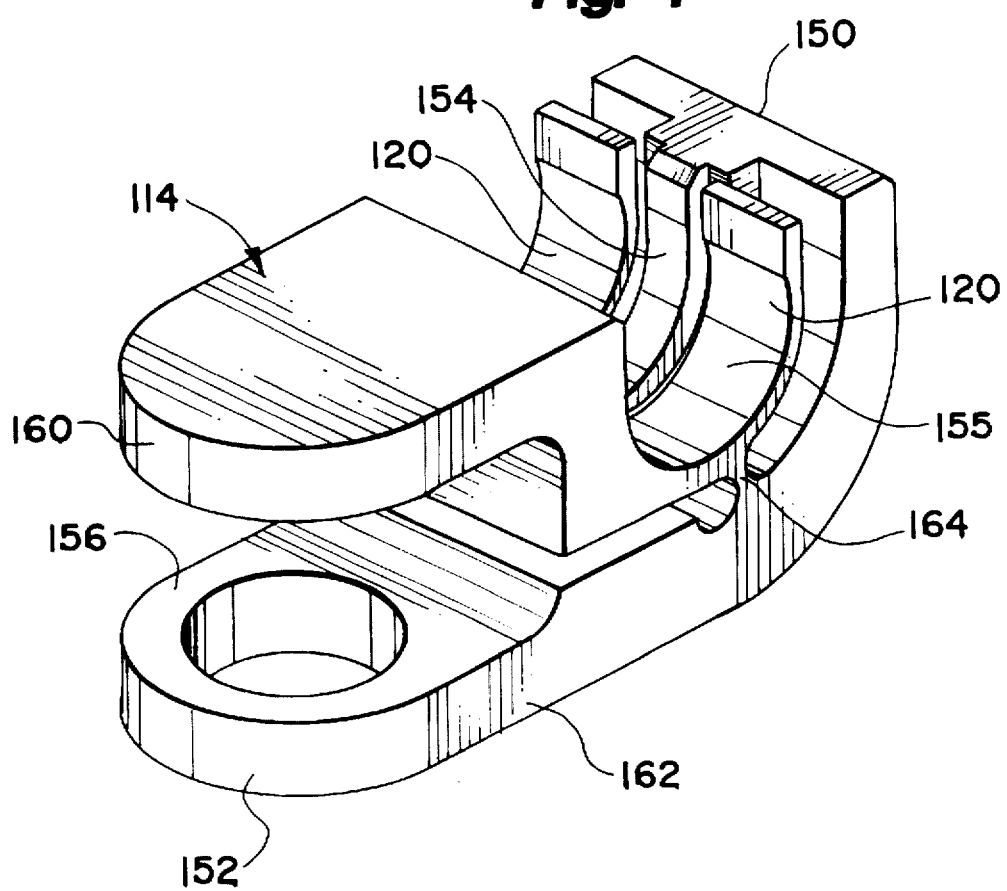
FIG. 4 is a perspective view of an alternative embodiment of a clamp member for use with the clamp of the present invention.

In an alternative embodiment, a second clamping member 114 has a second clamping end 150 and a second attachment end 152, as most clearly illustrated in FIG. 4. Proximate to the second clamping end 150, the second clamping member 114 has a second clamping surface 154 that defines a clamping slot 155. Proximate to the second attachment end 152, the second clamping member 114 has a second recess 156 formed therein. The second clamping surface 154 and the second attachment end 152 generally cause the second clamping member 114 to be generally divided into an upper leg portion 160, a lower leg portion 162, and a fulcrum portion 164, which extends between the upper and lower leg portions 160, 162. The fulcrum portion 164 allows the upper leg portion 160 to pivot with respect to the lower leg portion 162 so that the retractor support (not shown) may be clamped within the clamping slot 155.

The second clamping member 114 has an alternative mechanism for retaining objects adjacent to the second clamping surface 154 when the clamp is in the nonclamping position. With this embodiment, the second clamping member 114 is machined to produce two retaining legs 120 that are adjacent to at least a portion of the second clamping surface 154. The retaining legs 120 have a thickness sufficient to provide the legs with a spring force similar to the retaining clip 68 discussed with reference to FIGS. 1-3. The retaining legs 120 provide a spring force against the retractor support in a manner similar to retaining clip 68. Similarly to the clamp illustrated in FIGS. 1-3, the embodiment of FIG. 4 may also be removed from a retractor support by manual force when in the unclamped position.

When the second clamping member 114 is moved to a clamping position by moving apart the upper and lower leg portions 160, 162 proximate to the second attachment end 122, the upper and lower leg portions 160, 162 proximate to the second clamping end 120 move towards each other. This movement allows the object to be clamped with the second clamping surface 154.

Although the present invention has been described with reference to preferred embodiments, workers skilled in the art will recognize that changes may be made in form and detail without departing from the spirit and scope of the invention.

What is claimed is:

1. A clamping device comprising:
   a first clamping member fabricated from a unitary structure, wherein the first clamping member has a first clamping end, a first attachment end, and a first fulcrum portion located between the first clamping end and the first attachment end; and
   a second clamping member pivotally mounted with respect to the first clamping member so that the second clamping member engages the first clamping member proximate to the first attachment end, wherein the second clamping member is fabricated from a unitary structure, and wherein the second clamping member has a second clamping end, a second attachment end, and a second fulcrum portion located between the second clamping end and the second attachment end.

2. The clamping device of claim 1, wherein the second clamping member has a second clamping surface formed therein proximate to the second clamping end.

3. The clamping device of claim 2, and further comprising a retaining clip attached to the second clamping member proximate to the second clamping surface.

4. The clamping device of claim 2, and further comprising a retaining leg extending from the second clamping member adjacent to the second clamping surface.

5. The clamping device of claim 1, and further comprising an actuating mechanism that engages the first and second clamping members proximate to the first and second attachment ends, respectively, wherein the actuating mechanism allows the clamping device to be moved between an non-clamping position and a closed position.

6. The clamping device of claim 5, wherein the actuating mechanism comprises:
   a clamp handle that pivotally engages the first clamping member; and
   an actuating rod that engages the clamp handle and the second clamping member.

7. A clamping device comprising:
   a first clamping member fabricated from a unitary structure, wherein the first clamping member has a first clamping end, a first attachment end, and a first fulcrum portion located between the first clamping end and the first attachment end; and
   a second clamping member fabricated from a unitary structure, wherein the second clamping member has a second clamping end, a second attachment end, and a second fulcrum portion located between the second clamping end and the second attachment end, and wherein the second clamping member is pivotally mounted with respect to the first clamping member so that the second clamping member engages the first clamping member proximate to the first attachment end.

8. The clamping device of claim 7, wherein the second clamping member has a second clamping surface formed therein proximate to the second clamping end.

9. The clamping device of claim 8, and further comprising a retaining clip attached to the second clamping member proximate to the second clamping surface.

10. The clamping device of claim 8, and further comprising a retaining leg extending from the second clamping member adjacent to the second clamping surface.

11. The clamping device of claim 7, and further comprising an actuating mechanism that engages the first and second clamping members proximate to the first and second attachment ends, respectively, wherein the actuating mechanism allows the clamping device to be moved between an non-clamping position and a closed position.

12. The clamping device of claim 11, wherein the actuating mechanism comprises:
   a clamp handle that pivotally engages the first clamping member; and
   an actuating rod that engages the clamp handle and the second clamping member.

13. A clamping device for use in conjunction with a retractor support apparatus, the clamping device comprising:
   a first clamping member having:
      a first clamping surface formed therein; and
      a first fulcrum portion; and
   a second clamping member having:
      a second clamping surface formed therein; and
      a second fulcrum portion;
   wherein the first and second clamping members are pivotally mounted together so that:
      the first fulcrum portion is between the first clamping surface and a point at which the first clamping member pivotally mounts to the second clamping member; and
      the second fulcrum portion is between the second clamping surface and a point at which the second clamping member pivotally mounts to the second clamping member.

14. The clamping device of claim 13, wherein the second clamping member is fabricated from a unitary structure.

15. The clamping device of claim 14, and further comprising a retaining clip attached to the second clamping member proximate to the second clamping surface.

16. The clamping device of claim 14, and further comprising a retaining leg extending from the second clamping member adjacent to the second clamping surface.

17. A clamping device for use in a retractor support having a cylindrical shaped support portion, the clamping device comprising:
   a first clamping member having a first clamping surface formed therein; and
   a second clamping member having a second clamping surface defining a clamping slot, wherein the clamping slot is configured to receive the cylindrically shaped support portion of the retractor support and wherein the second clamping member further includes a spring element for securing the second clamping member onto the cylindrically shaped support portion of the retractor support with sufficient force to retain the clamping member in a selected rotational position with respect to the retractor support.

18. The clamping device of claim 17, and further comprising a retaining clip attached to the second clamping member proximate to the second clamping surface.

19. The clamping device of claim 17, and further comprising a retaining leg extending from the second clamping member adjacent to the second clamping surface.

* * * * *